United States Patent [19]

Verderber

[11] Patent Number: 5,457,611
[45] Date of Patent: Oct. 10, 1995

[54] AMBIENT AIR COOLED LIGHT EMITTING INSTRUMENT

[75] Inventor: Gregory R. Verderber, Cincinnati, Ohio

[73] Assignee: Gregg Laboratories, Inc., Cincinnati, Ohio

[21] Appl. No.: 89,251

[22] Filed: Jul. 9, 1993

[51] Int. Cl.$^6$ ........................................................ A61B 1/07
[52] U.S. Cl. ............................ 362/32; 362/109; 362/804; 362/138; 362/373; 362/294; 433/29; 433/30
[58] Field of Search ........................... 362/373, 32, 109, 362/138, 218, 263, 264, 294, 804, 345, 310, 267; 128/21, 22, 23, 16, 13; 606/15, 17; 607/88, 90, 92, 93; 433/29, 30, 31

[56] References Cited

U.S. PATENT DOCUMENTS

| | | | |
|---|---|---|---|
| 2,297,799 | 10/1942 | Pifer | 362/804 |
| 2,424,437 | 7/1947 | Dent | 16/116 |
| 2,635,280 | 4/1953 | Baca | 16/116 |
| 3,216,052 | 11/1965 | Hill | 16/116 |
| 3,336,462 | 8/1967 | Fuller | 219/227 |
| 3,371,202 | 2/1968 | Moore et al. | 362/804 |
| 3,634,938 | 1/1972 | Hutchinson | 32/27 |
| 4,171,572 | 10/1979 | Nash | 32/27 |
| 4,209,877 | 7/1980 | Colasent | 16/116 R |
| 4,281,366 | 7/1981 | Wurster et al. | 362/32 |
| 4,334,863 | 6/1982 | Magid et al. | 433/29 |
| 4,403,957 | 9/1983 | Mössle et al. | 433/29 |
| 4,435,636 | 3/1984 | Royston | 219/230 |
| 4,477,252 | 10/1984 | Lieb et al. | 433/29 |
| 4,534,732 | 8/1985 | Strohmaier | 433/29 |
| 4,568,281 | 2/1986 | Harvey et al. | 433/30 |
| 4,568,284 | 2/1986 | Stankiewicz | 433/126 |
| 4,578,034 | 3/1985 | Shibata et al. | 433/29 |
| 4,655,709 | 4/1987 | Fleer | 433/29 |
| 4,704,660 | 11/1987 | Robbins | 362/32 |
| 4,798,934 | 1/1989 | Boyer | 219/233 |
| 4,907,135 | 3/1990 | Tarrson et al. | 362/109 |
| 4,938,692 | 7/1990 | Castellini | 433/29 |
| 4,975,058 | 12/1990 | Woodward | 433/126 |
| 5,029,056 | 7/1991 | Patterson, Jr. | 362/267 |
| 5,055,044 | 10/1991 | Kuhn | 433/126 |
| 5,057,015 | 10/1991 | Fleer | 433/126 |
| 5,076,660 | 12/1991 | Messinger | 385/119 |
| 5,139,421 | 8/1992 | Verderber | 433/31 |

FOREIGN PATENT DOCUMENTS 2603513  8/1977  Germany ............................. 362/804

Primary Examiner—Ira S. Lazarus
Assistant Examiner—Sara Sachie Raab
Attorney, Agent, or Firm—Jerrold J. Litzinger

[57] ABSTRACT

An ambient air cooled high intensity light emitting instrument in which the lamp is contained in a heat sink mounted within the housing. The housing contains a plurality of vent holes which circumscribe the heat sink. As heat from the light is conducted along the heat sink when the instrument is in use, the heat emanates into the chamber surrounding the heat sink, and rises through the vent holes to the surrounding atmosphere, generating a thermal current which replaces the departing hot air with cooler air from the atmosphere.

18 Claims, 3 Drawing Sheets

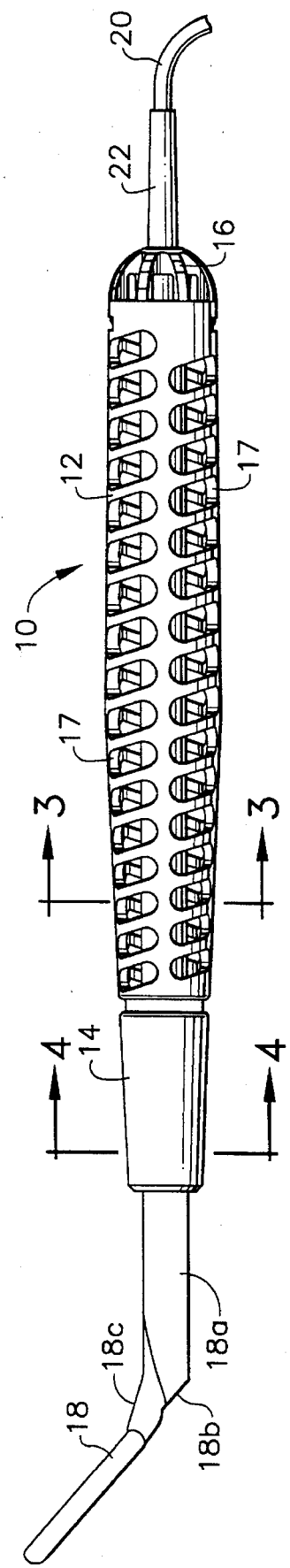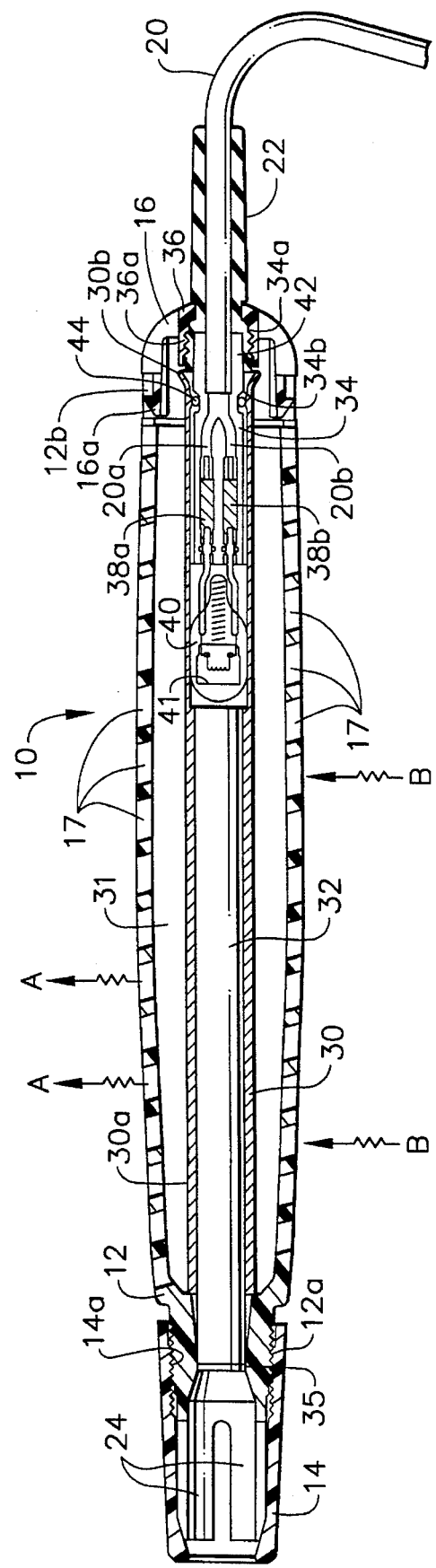

5,457,611

AMBIENT AIR COOLED LIGHT EMITTING INSTRUMENT

BACKGROUND OF THE INVENTION

1. Field of the Invention

The present invention relates generally to light emitting instruments and, in particular, to an improved ambient air cooled high intensity light emitting instrument.

2. Description of the Prior Art

Many opportunities for visual inspection require prolonged continuous use of light in order to adequately illuminate the area to be inspected. Hand held medical and dental light sources which provide illumination for inspection or examination are well known and have been utilized for many years. Specific examples of such devices include ophthalmascopes, otoscopes, retinoscopes, and other similar instruments. In these hand held devices, the handle generally houses the light source. It is advantageous to mount the lamp within the instrument rather than in a remote location, requiring the use of additional transmission means such as fiber optics, to direct the light to the desired location. Although a remote light source is easy to cool, it usually results in a relatively inflexible fiber optic cable, significantly limiting the maneuverability of the instrument and increasing the overall cost of the instrument.

Recently, high intensity light sources, such as halogen or krypton gas filled lamps have been developed to provide significantly more light for hand held dental and medical instruments. This increase in light intensity, often two to three times greater than that provided by ordinary vacuum lamps of the same size, greatly improves the performance of these instruments. In addition, vacuum lamps progressively deteriorate in both quantity and quality of light emission as the lamp ages due to tungsten particles which are deposited on the envelope of the lamp. A halogen lamp however, provides a reasonably consistent quantity and quality of light emission over its life, due in part to the extreme lamp skin temperature (250°–300° C.) which causes tungsten particles deposited on the envelope of the lamp to vaporize and redeposit on the tungsten filament.

Unfortunately, this extreme heat generated by high intensity lamps can often lead to other problems for hand held instruments. Obviously, heat buildup within the handle will cause discomfort to the user of the instrument. This problem becomes exaggerated as the duty cycle for the instrument increases. Some dental or surgical procedures require a hand held instrument to be used continuously for extended periods of time, such as an hour or more. Other heat related problems inherent in these instruments include accelerated deterioration of the lamp and instrument materials, and potential injury to the person on whom the instrument is used.

The problem of heat build up in hand held instruments using high intensity lamps has been addressed several times in the prior art. U.S. Pat. Nos. 4,334,863; 4,477,252; and 5,033,960 all teach specific solutions to the problem of heat generation within the handle of dental instruments. U.S. Pat. Nos. 4,334,863 and 4,477,252 each teach a dental handpiece in which air used to drive the handpiece is also used to cool the heat generated by the fiber optic system mounted within the handpiece, while U.S. Pat. No. 5,033,960 teaches a device which channels exhaust air from the dental handpiece to flow laterally into the lamp socket to cool the lamp used in its fiber optic system.

Another problem associated with the use of hand held medical and dental instruments is contamination. It is well known in the practice of medicine and dentistry that great care must be taken to protect against diseases transmitted by cross contamination. Many serious diseases, including hepatitis and the deadly disease AIDS, can be transmitted by cross contamination. The most effective method of controlling cross contamination when using medical instruments is sterilization. The usual method of sterilization of instruments of this type is autoclaving. The autoclaving procedure requires subjecting the instrument to an environment of pressurized steam at 250° F. for an extended period of time. One potential problem in light emitting instruments after autoclaving is residual moisture, which could cause a short in the electrical circuitry of the instrument during operation. Therefore, is important that the circuitry of the instrument is adequately sealed to prevent both contamination and autoclaving steam from contacting the circuitry.

However, while sealing the circuitry areas of the instrument protects it from residual moisture, it also acts to keep heat trapped within this area. Thus, the ability of the instrument to dissipate heat adequately is much more imperative.

SUMMARY OF THE INVENTION

It is therefore an object of the present invention to provide a high performance, hand held instrument having the ability to dissipate substantial heat generated by a high intensity light source and which does not become uncomfortable to grip during use.

It is also an object of the present invention to provide an instrument having a handle which does not significantly overheat, causing components and/or materials to fail prematurely.

It is also an object of the present invention to provide an instrument having a handle which does not require compressed air, liquids, or a fan for cooling.

It is a further object of the present invention to provide a light emitting instrument which is designed such that it can be comfortably manipulated by the user.

Still another object of the present invention is to provide an improved light emitting instrument that can be economically manufactured, and still be effectively sterilized by methods commonly employed in the health care industry.

BRIEF DESCRIPTION OF THE DRAWINGS

FIG. 1 is a plan view of a high intensity light emitting instrument employing the present invention.

FIG. 2 is a longitudinal cross-sectional view of the body of instrument shown in FIG. 1.

DETAILED DESCRIPTION OF THE PREFERRED EMBODIMENTS

Figure 3:
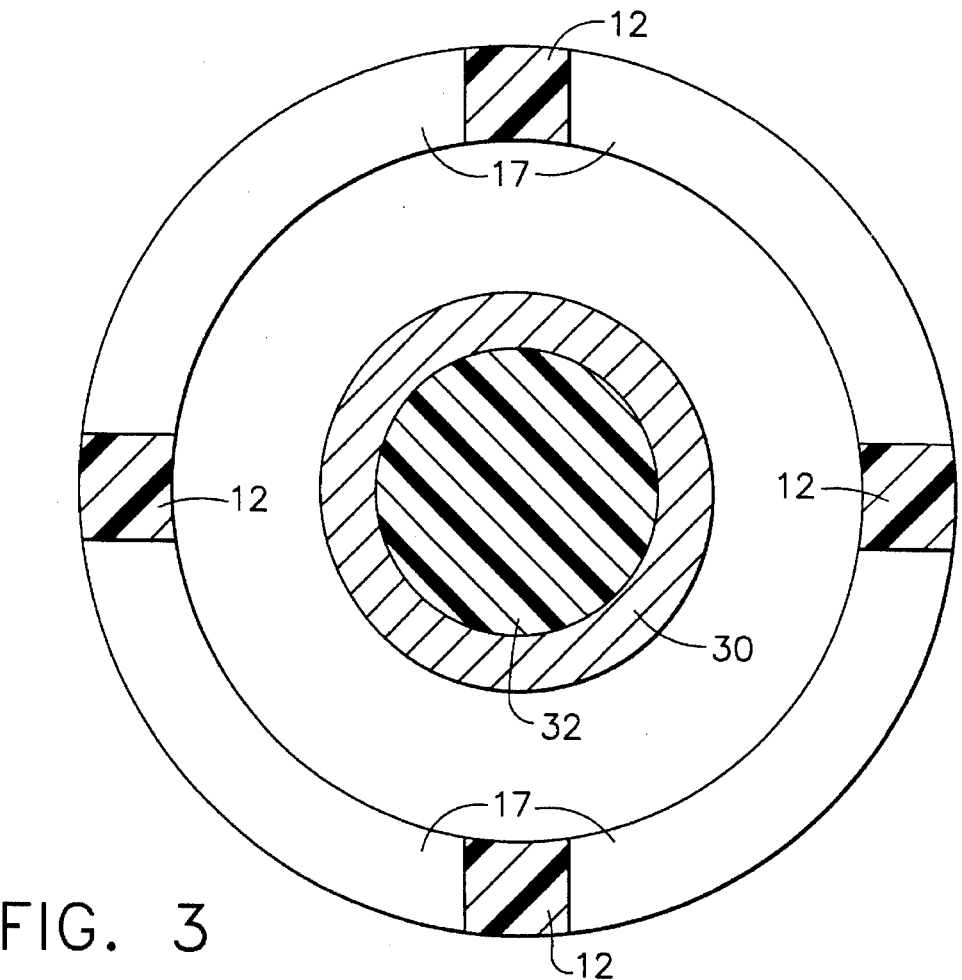
FIG. 3 is a cross-sectional view of the instrument shown in FIG. 1 taken along line 3—3.

Referring now to FIG. 1, a high intensity light emitting instrument is generally indicated at 10. Instrument 10 consists of a body section 12, a front end cap 14 and a rear end cap 16. Rear end cap 16 contains an indented annular surface 16a for attachment purposes. Body 12 and caps 14, 16 are preferably constructed from plastic or other low heat absorbing materials. Body section 12 contains a plurality of parallel slots or apertures 17 through the wall of body 12 which are arranged in two rows on both sides of instrument 10. Inserted into the front end of instrument 10 is a mirror 18 having a shank portion 18a, a heel portion 18b, and a face portion 18c. Mirror 18 is of the type described in U.S. Pat. No. 5,139,421, in which light transmitted into shank portion 18a is emitted from heel portion 18b and face portion 18c on both sides of mirror 18. Any selective light transmission implement, such as a transilluminator or the like, may be used in place of mirror 18 with instrument 10. Finally, an electrical cord 20 containing a pair of wires 20a and 20b is inserted into rear end cap 16 using a cord grip 22 to provide the energy to operate instrument 10.

Figure 4:
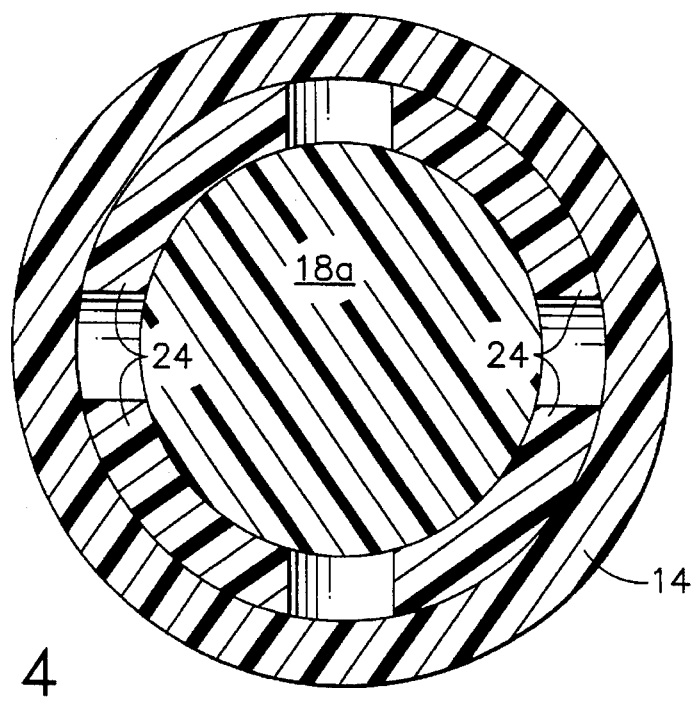
FIG. 4 is a cross-sectional view of the instrument shown in FIG. 1 taken along line 4—4.

The internal components of instrument 10 can be viewed most clearly in FIG. 2. The front end of body 12 contains a threaded section 12a, and also a plurality of collet-like segments 24 (see also FIG. 4) while the rear end of body 12 contains an extended annular surface 12b. Front end cap 14 contains an internally threaded section 14a corresponding to threaded section 12a of body 12. When mirror 18 (or any light transmission implement) is inserted into the end of body 12, as cap 14 is rotated onto the end of body 12 by virtue of the mating threaded sections 14a and 12a, segments 24 are caused to tighten around the shank portion 18a of mirror 18, holding mirror 18 securely in position within body 12 of instrument 10. This allows for a variety of implements to be easily interchanged when using instrument 10.

A heat sink 30 having a forward end 30a and a flared rear end 30b is located within the central region of body 12. The area within body 12 surrounding heat sink 30 forms an ambient air chamber 31. Heat sink 30 is a tubular member manufactured from a thermally conductive material, such as aluminum or copper (which are highly efficient at conducting heat). A light transmission rod 32 is located within the front end of heat sink 30, which rod is held firmly within heat sink 30 by means of a suitable adhesive, such as a high temperature resistant glue, or by means of an interference fit. Located within the rear end of heat sink 30 is a lamp assembly unit 34 containing a threaded portion 34a and an annular channel 34b. Rod 32 may be composed of a high quality quartz glass, or any other material having high quality light transmission capabilities.

Heat sink 30 is secured in its proper position within body 12 by virtue of a support 36. Support 36 contains an internally threaded section 36a, which corresponds to threaded section 34a of lamp unit assembly 34. When instrument 10 is assembled, cord grip 22, which extends through end cap 16, is positioned within support 36 in contact with unit 34. As support 36 is rotated onto the end of unit 34 by virtue of the mating threaded sections 36a and 34a, heat sink 30 (in addition to unit 34 and rod 32) are positioned within the rear end of body 12, and is held in its proper position by virtue of annular surface 16a located on end cap 16 cooperating with surface 12b of body 12. The front end of heat sink 30 is secured in its proper position by virtue of rod 30 cooperating with an inner surface 35 at the front end of body 12 adjacent collet segments 24.

Electrical cord 20 is received within lamp assembly unit 34 at section 34a, and wires 20a and 20b are attached to a pair of electrical connectors 38a and 38b respectively by any conventional means capable of withstanding high temperatures. A high intensity lamp 40 is connected to the opposite ends of connectors 38a and 38b. Lamp 40 is positioned within heat sink 30 at close approximation to rod 32, and contains a lens 41 for focusing its light into the end of rod 32.

Lamp unit assembly 34 is sealed by the use of a potting compound or other high temperature resistant elastomeric material 42 which serves to bond cord 20, wires 20a and 20b, connectors 38a and 38b and lamp 40 into a single moisture resistant unit. This structure allows for easy replacement of the entire unit when necessary. In addition, an elastomeric seal or O-ring 44 constructed of heat resistant material is inserted into annular channel 34b, and cooperates with heat sink 30 to further inhibit moisture from contaminating the interior of heat sink 30 or lamp 40.

The advantages of a light emitting device embodying the present invention will now be described. Referring again to FIGS. 1 and 2, when cord 20 is connected to suitable current generating means, electrical current flows thorough wires 20a and 20b, connectors 38a and 38b, and ultimately to lamp 40, causing lamp 40, which is a high intensity lamp, to illuminate. High intensity light passes through focal lens 41 into the end of rod 32. As rod 32 is preferably composed of a high quality light transmission material, essentially all of the light generated by lamp 40 is transmitted along rod 32 into shank portion 18a of mirror 18, where it is ultimately transmitted in the manner taught in U.S. Pat. No. 5,139,421. Any alternative light transmission means, such as a transilluminator, would emit the light as it passes through the front end of rod 32.

As lamp 40 emits high intensity light, it also generates a considerable amount of heat. Since lamp 40 is mounted within heat sink 30, the heat is conducted along the longitudinal axis of heat sink 30 in both directions, and is dissipated from its surface into ambient chamber 31 within body 12 surrounding heat sink 30.

When lamp 40 is initially illuminated, the ambient air in chamber 31 within body 12 is at approximately the same temperature as the environment surrounding light emitting instrument 10. As lamp 40 continues to generate high intensity light and its resultant heat (which is conducted along heat sink 30), the temperature of heat sink 30 rises above the temperature of the ambient air within body 12. As a result of the thermodynamic properties of heat sink 30, heat is transferred from sink 30 to the surrounding air within chamber 31 inside body 12. As the air temperature within chamber 31 rises, thermal currents are generated, due to the fact that warmer air is lighter and will rise and displace the cooler air, which is heavier. Thus, if instrument 10 is in the orientation shown in FIGS. 1 and 2, the heated air within chamber 31 within body 12 will exit chamber 31 through the plurality of apertures 17 formed in body 12 in the direction of arrow A into the surrounding environment. The action of warmer air exiting instrument 10 in the direction of arrows A causes air in the surrounding environment to enter chamber 31 within body 12 from the underside of instrument 10, as shown by arrows B in FIG. 2. This continuous movement of air through body 12 resulting from the unique structure of instrument 10 automatically cools instrument 10 without the necessity of using additional mechanical devices to generate cooling fluids, adding complexity and cost to the instrument, while further limiting its versatility.

Figure 5:
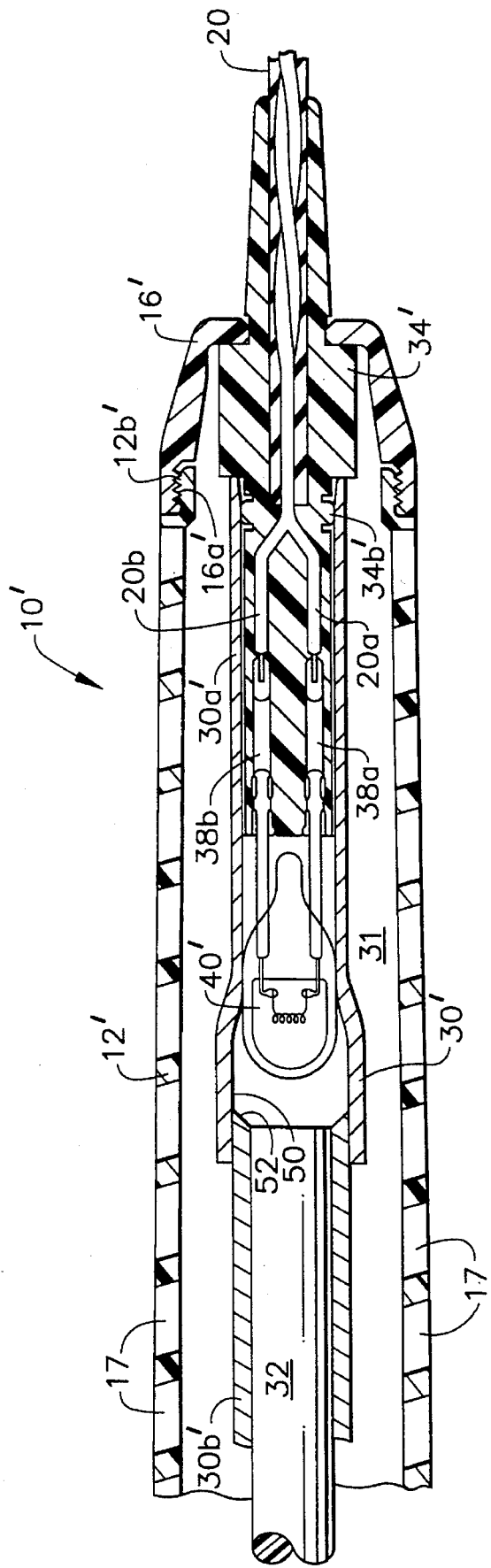
FIG. 5 is a fragmentary cross-sectional view of an alternate embodiment employing the present invention.

Referring now to FIG. 5, a second embodiment of a light emitting instrument embodying the present invention is shown. In this embodiment, like parts have been given like numerals.

Instrument 10' is essentially the same as instrument 10 of FIGS. 1–4, except for heat sink 30', lamp 40', and lamp unit assembly 34'. Heat sink 30' is composed of two sections 30a' and 30b', which are secured together using a heat resistant adhesive or any other suitable attachment means which will insure a leak-proof fit. Lamp 40' is a high intensity lamp, but does not contain an internal lens similar to lamp 40. Thus light emitted from lamp 40' is non-coherent and is not focused on the end of light transmission rod 32, as light is emitted from lamp 40' in all directions. Therefore a reflective coating 50 is applied to the inner surface of section 30a' of heat sink 30' for gathering these non-coherent light beams, and coating 50 focuses them on the end of light transmission rod 32. A reflective coating 52 is applied to the end of section 30b' of heat sink 30' for reflecting light beams which would otherwise miss the end of rod 32 back to reflective coating 50 where they can be refocused at the end of rod 32. The arrangement permits the effective use of a non lens-ended high intensity lamp by using reflective surfaces to focus the non-coherent light beams into the light transmission rod.

The embodiment shown in FIG. 5 uses a one piece molded lamp unit assembly 34' made from a high temperature resistant elastomeric material to bond cord 20, wires 20a and 20b, and connectors 38a and 38b into a single unit. Assembly 34' contains an annular ridge 34b' to form an effective seal within heat sink 30' to keep out moisture, and is held in place within instrument 10' by rear end cap 16', which has a threaded section 16a' which engages a threaded section 12b' of body 12'.

In the above description, and in the claims which follow, the use of such words as "up", "down", "forward", "rearward", "vertical", "horizontal", and the like, is in conjunction with the drawings for purposes of clarity. As will be understood by one skilled in the art, the device can assume any orientation during use, depending upon the application to which it is directed.

While the present invention has been shown and described in terms of preferred embodiments thereof, it will be understood that this invention is not limited to any particular embodiment and that many changes and modifications may be made without departing from the true spirit and scope of the invention as defined in the appended claims. For example, the heat sink may be formed with the external circumference fluted or finned so as to increase surface area contact between the heat sink and the surrounding air in the chamber to increase the dissipation efficiency of the heat sink. In addition, the light source used may be a laser adapted for use in a hand held instrument.

What is claimed is:

1. A hand held light emitting instrument, comprising:

a housing having an interior chamber and an outer gripping surface for handling by a user, said housing being surrounded by an external atmosphere;

a member, located within said housing, containing a light source and a light transmission rod in close approximation to said light source, for transmitting light from the instrument, with said member being thermodynamically isolated from said interior chamber of said housing;

means, located through said housing, for venting the interior chamber of said housing to the external atmosphere surrounding said housing;

whereby heat generated by said light source emanates from said member into the interior chamber of said housing and is transferred to the external atmosphere surrounding said housing through said vent means, allowing said outer gripping surface to remain cool such that the instrument can be comfortably handled by a user.

2. The instrument of claim 1, wherein said member comprises a heat sink.

3. The instrument of claim 2, wherein said heat sink consists of a cylinder constructed from aluminum.

4. The instrument of claim 2, wherein said light source comprises a high intensity light source.

5. The instrument of claim 4, wherein said source is a halogen lamp.

6. The instrument of claim 1, wherein said light source contains a focal lens for directing light into said light transmission rod.

7. The instrument of claim 1, wherein said housing is constructed from a low heat absorbing material.

8. The instrument of claim 1, wherein said member is thermodynamically isolated from the interior of said housing using a seal constructed from heat resistant material.

9. The instrument of claim 1, wherein said venting means comprises a plurality of apertures along said housing.

10. A hand held light emitting instrument, comprising:

a housing, surrounded by an external atmosphere, having an interior chamber and an outer surface capable of being held by a user, said housing further having a forward light emitting end and a rearward end;

a hollow member, thermodynamically isolated from the interior chamber of said housing, positioned within said housing from said forward end to said rearward end;

a light source, located within said member;

a light transmission rod, positioned within said member between said light source and said forward end;

vent means through said housing for communicating the interior chamber within said housing with the atmosphere surrounding said housing; and means for activating said light source; such that when said light source is activated, light is transmitted from said light source through said light transmission rod and to said forward light emitting end of said housing, and heat generated by said light source emanates from said member into said interior chamber and passes through said vent means into said surrounding atmosphere, whereby cooling said outer surface such that said instrument can be comfortably held by a user.

11. The instrument of claim 10, wherein said member is a heat sink and said light source is a high intensity lamp.

12. The instrument of claim 10, wherein said member is thermodynamically isolated from the interior of said housing using an elastomeric seal between said member and said rearward end.

13. The instrument of claim 12, wherein said member comprises a cylindrical heat sink composed of material having thermal conductivity properties.

14. The instrument of claim 10, wherein said vent means comprises a plurality of apertures arranged along said housing.

15. The instrument of claim 14, wherein said apertures are arranged in a plurality of rows extending from said forward end to said rearward end.

16. The instrument of claim 10, wherein said member consists of a first section containing said light source coupled to a second section containing said light transmission rod.

17. The instrument of claim 10, further comprising a light directing apparatus positioned at said forward end of said housing adjacent said light transmission rod.

18. A hand held light emitting instrument, comprising:

a housing, having a forward light emitting end and a rearward end, and an outer surface capable of being held by a hand of a user;

a hollow tubular member, positioned within said housing from said forward end to said rearward end to form an air chamber between said housing and said tubular member, which chamber is thermodynamically isolated from the interior of said member;

a light source, located within said tubular member;

a light transmission rod, located within said tubular member between said light source and the forward end of said housing, for emitting light from the instrument;

and a plurality of apertures, located in said housing; whereby heat generated by said light source emanates from said tubular member into said chamber within said housing surrounding said tubular member and is removed from said chamber through said apertures in said housing by thermal currents generated as the heat rises out through said apertures.

* * * * *